US00PP10370P

United States Patent [19]

Panzer

[11] Patent Number: Plant 10,370

[45] Date of Patent: May 5, 1998

[54] AZALEA—'JEAN PANZER'

[75] Inventor: Fred Panzer, Beaverton, Oreg.

[73] Assignee: Panzer Nursey, Inc., Beaverton, Oreg.

[21] Appl. No.: 377,934

[22] Filed: Jan. 25, 1995

[51] Int. Cl.[6] ..... A01H 5/00

[52] U.S. Cl. ..... Plt./57

[58] Field of Search ..... Plt./55–57

[56] References Cited

PUBLICATIONS

Lee, F. P. (listings for) "Jeanne", *The Azalea Book*, 2nd Ed., 1965, D. Van Nostrand Co., Inc., Princeton, N.J., pp. 211, 276.

Leach, D. G., "Breeding Rhododendrons" *Rhododendrons of the World* Charles Scribner'2 Sons, 1961, p. 387.

*Primary Examiner*—James R. Feyrer

*Attorney, Agent, or Firm*—Chernoff, Vilhauer, McClung & Stenzel

[57] ABSTRACT

A new variety of azalea characterized by its sturdy and generally upright growth habit, its Tea Rose-shaped red flowers, and its unusually early spring flowering.

2 Drawing Sheets

BACKGROUND AND SUMMARY OF THE INVENTION

This new variety of azalea was discovered in 1991 growing on a potted plant at the inventor's commercial nursery located in Beaverton, Oreg. The new variety is a spontaneous mutation of the "Peace" azalea, discovered as a limb sport. Subsequent asexual propagation by cuttings at the same location has demonstrated that the below-described valuable characteristics are genetically stable and hold true from generation to generation. The Peace azalea is a florist azalea of the Kerrigan hybrid species and is known to be available only from a limited number of commercial greenhouse growers in the Pacific Northwest.

The 'Jean Panzer' azalea and its parent Peace azalea are identical in all aspects except flower color. The 'Peace' flower is white compared to the red group #52B color of the 'Jean' flower.

The forcing requirements and natural flower dates of the Peace azalea and the 'Jean' azalea are identical. Neither variety has any fragrance. Flower fertility is unknown for either variety. The outdoor reaction for either variety is not known as both varieties are florist azaleas and are always grown in a greenhouse.

DETAILED DESCRIPTION OF THE DISCLOSURE

Figure 1:
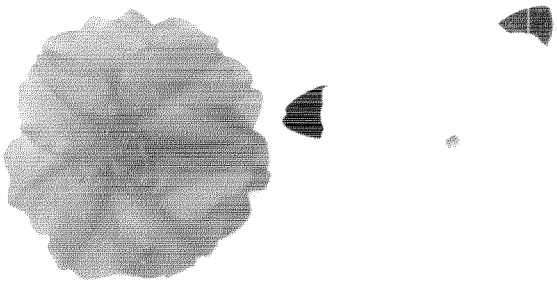
FIG. 1 shows the flower with the flower of the parent 'Peace'.
Figure 2:
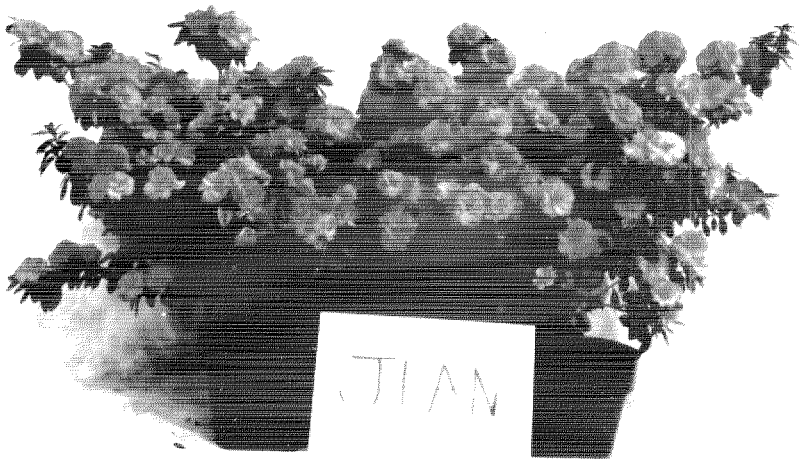
FIG. 2 shows the plant potted.
Figure 3:
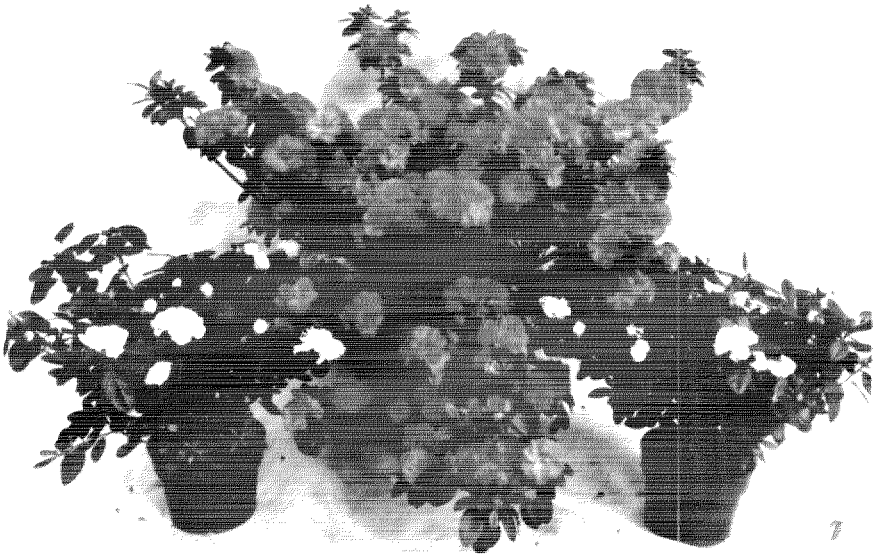
FIG. 3 shows the blooming plant with the parent 'Peace'.

The following is a detailed description of the new azalea variety based upon observations made in greenhouses located at the inventors nursery in Beaverton, Oreg. Where possible, precise color assessment has been made with reference to The Royal Horticulture Society Color Chart:

Origin: Origin: 'Peace', origin of the parent unknown.

Classification:

*Botanical.*—Family: Ericaceae. Genus: Rhododendron. Species: Kerrigan Hybrid Group.

*Cultivar.*—'Jean Panzer'

*Commercial.*—Hybrid azalea.

*Market class.*—Florist azalea.

Form: Upright to spreading bush.

Height: Medium, 7 to 15 inches is the generally accepted commercial height; its natural height would be greater.

Growth: Medium grower, sturdy and generally upright; under greenhouse conditions will grow from a 2" cutting to a 10"×10" market-size plant in 30 months.

Branching: Well branched, with prolific branching tendencies.

Stem: Younger shoot color is yellow green group #144A, #144B or #144C; older stems are a woody bronze color.

Foliage: Abundant, generally alternate similar to the 'Helmut Vogel' azalea; evergreen, foliage is retained through the year.

*Leaf size.*—¾" to 1" across, 1" to 2" from base to apex, petiole approximately ¼" long.

*Leaf shape.*—Elliptic to oblanceolate and entire with a mucronate apex and an obtuse base.

*Texture.*—Slightly pubescent.

*Aspect.*—Glossy.

*Ribs and veins.*—Alternately pinnate.

*Color.*—Upper side—Young leaves: Yellow green group #143A to #144A. Older leaves: Green group #137A to #139A. Under side—Young leaves: Yellow green group #146B to #146D. Older leaves: Green group #138A to #138B.

The Bud

Form: Ovate and pointed.

Size: ¼" to ¾" long, ¼" to ½" diameter.

Opening rate: Buds open slowly in early spring.

Opening bud color: When sepals first divide petals are in red group #51A; when petals begin to unfurl, petals are red group #52B.

Sepals color:

*When tight bud.*—Yellow green #154C or #154D.

Calyx: Funnel-shaped with deep clefts, small, and pubescent.

Peduncle: Yellow green #144B, strong and upright, ¼" to ½" long, and pubescent.

The Flower

Blooming habit: Flowering is in early spring.

Size: About 2" to 3" in diameter and about 1" in depth, the flower flattens out as it opens.

Shape: Tea rose shape.

Inflorescence: Umbel, in clusters of 2–6 flowers.

Petals: Multi-petaled usually in groups of five.

*Arrangement.*—Imbricated petals, double flowers with 3–10 corollas that overlap alternately.

*Form.*—Corolla generally gamopetalous; fused at the base.

*Texture.*—Soft and delicate.

*Aspect.*—Intense, semi-glossy.

*Color.*—Petals red group #52B; the flower fades to #52C.

*Peduncle.*—Yellow-green #144B, strong and upright, ¼" to ½" long, and pubescent.

Persistence: Flowers last for over a month, hang on and dry.

Reproductive organs: Pistil usually single, ovary superior and hairy, stamens usually not present.

Disease tolerance: Very disease resistant.

Hardiness: Estimated hardy to 25° to 30° F.

What is claimed is:

1. A new and distinct azalea plant substantially as herein shown and described, characterized particularly by its tea rose-shaped red flowers.

* * * * *